United States Patent [19]

Hoogendoorn et al.

[11] Patent Number: 4,602,639
[45] Date of Patent: Jul. 29, 1986

[54] METHOD AND APPARATUS FOR CONTACTLESS MEASUREMENT OF CHARGE CONCENTRATIONS AND POTENTIAL DIFFERENCES IN BIOLOGICAL ORGANISMS

[75] Inventors: Dirk Hoogendoorn, Hilversum; Jacobus C. L. Van Peppen, Delft; A. Michael Stuivenwold, Wassenaar, all of Netherlands

[73] Assignee: Mardice Holding S.a.r.l., Luxembourg, Luxembourg

[21] Appl. No.: 509,651

[22] Filed: Jun. 30, 1983

[30] Foreign Application Priority Data

Jul. 1, 1982 [LU] Luxembourg ............................ 84250

[51] Int. Cl.$^4$ ............................................. A61B 17/36
[52] U.S. Cl. ..................................... 128/639; 128/734; 128/303.13
[58] Field of Search ............. 128/1.3, 1.4, 734, 419 R, 128/783, 303.13, 303.14, 303.17, 639, 642, 733, 722; 324/60 C

[56] References Cited

U.S. PATENT DOCUMENTS

| | | | |
|---|---|---|---|
| Re. 31,097 | 12/1982 | Vas et al. | 128/700 |
| 3,323,515 | 6/1967 | Foner et al. | 128/639 |
| 3,744,482 | 7/1973 | Kaufman et al. | 128/639 |
| 4,200,104 | 4/1980 | Harris | 128/303.14 |
| 4,303,073 | 12/1981 | Archibald | 128/303.13 |
| 4,387,714 | 6/1983 | Geddes et al. | 128/303.13 |

FOREIGN PATENT DOCUMENTS

1281573 10/1968 Fed. Rep. of Germany .
2928826 2/1981 Fed. Rep. of Germany .

*Primary Examiner*—Edward M. Coven
*Attorney, Agent, or Firm*—Fishman & Dionne

[57] ABSTRACT

Apparatus and a method are presented for contactless measurement of charge concentrations and potential differences in biological organisms, with the electrode being spaced from the organism. Relative movement between the organism and the probe results in alteration of the electrostatic field which is measured in an external circuit to determine potential differences in the organism.

21 Claims, 14 Drawing Figures

METHOD AND APPARATUS FOR CONTACTLESS MEASUREMENT OF CHARGE CONCENTRATIONS AND POTENTIAL DIFFERENCES IN BIOLOGICAL ORGANISMS

BACKGROUND OF THE INVENTION

This invention relates to a method and apparatus for the contactless measurement of charge concentrations and potential differences in biological organisms, particularly in humans, animals and plants.

It is known that under certain conditions electrical charge concentrations and potential differences exist and occur in biological organisms. Pathological, convalescent, informational and other processes take place in biological organisms in accordance with an electrical direct-current system in which electrical charge concentrations and potential differences occur during the course of and on the occasion of such processes.

The electrical potential differences in a biological organism provide information on various life processes in the biologial organisms. For example, in the case of plants, trees and shrubs it is known that the parts exposed to the rays of the sun have a higher electrical potential than those situated in the shade. Further details are to be found in "The Basic Biological Data Transmission and Control System Influenced by Electrical Forces" by R. O. Becker, in "Annals of the New York Academy of Sciences"—vol. 238—11/10/74—pp. 236-241.

Measurement of these potential differences can be made by apparatus by which electrical fields can be traced and their magnitude determined. There are a number of such devices in existence in the prior art, but they are all deficient due to the construction of the measuring probe, and they are inaccurate.

The desirability of contactless electrodes for measuring potentials in biological organisms is recognized. From the article in IEE—"Transactions on Biomedical Engineering(US)"—Vol. BME—27—No. 12—Dec. 1980—B. C. Towe: "An Air Ionization Biopotential Electrode"—pp. 733-736—measuring electrodes are known by which surface potential differences can be measured without contact. The use of such electrodes, however, necessitates the ionization of air between the surface of the organisms and the electrode to form an electrically conductive medium. In this particular case the ionization is obtained by means of an ionizing radiation source present on the electrode, particularly by a 100 uCi-radioactive polonium-210-radioisotope which emits X-rays.

Also, from the article in IEE Transactions on Biomedical Engineering, Vol. BME-18, No. 2, March 1971, "Anodic Insulated Tantalum Oxide Electrocardiograph Electrodes", pp. 162-164, by C. H. Lagon et al, insulating measuring electrodes are known which serve to record measuring values intended for ECG. The insulation consists of a tantalum oxide film. This measuring electrode is a contact electrode of a particular kind which is used for ECG.

SUMMARY OF THE PRESENT INVENTION

The above discussed and other deficiencies of the prior art are eliminated or reduced by the apparatus and method of the present invention. In accordance with the present invention, new and novel apparatus and a method are presented by means of which the contactless measurement of charge concentrations and electrical differences of potential in biological organisms can be carried out. The new apparatus operates accurately and includes new types of contactless capacitance probes.

In accordance with the present invention, a capacitor is formed by a measuring electrode which is held over the surface of the organism without contact and which is one plate of the capacitor and by the surface of the organism itself which is the other plate of the capacitor. Continuous alterations in the electrostatic field between the capacitor plate is brought about by relative movement between the capacitor plates, and the resulting changes in the charge are measured and evaluated, these being an expression of the charge concentrations prevailing in the biological organism.

According to the measuring process of the present invention, when the capacitor formed by the measuring electrode and the surface of the organism is connected to an external circuit, an electrical current is created by which the charge of the measuring electrode is changed to that of the surface of the organism. A change in the electrostatic field in the capacitor consequently causes a corresponding change in the charge on the measuring electrode. Such a change therefore results in a new current flowing through the external circuit. This current is a measure of the change in the charge and thus of the difference in potential in the organism.

To carry out the process of the present invention, novel measuring apparatus is also provided. The apparatus includes a probe of a screened electrically conductive measuring electrode exposed to and communicating with electrostatic fields via a suitable window provided in the screening; circuits for electrically connecting the conductive measuring electrode to a reference potential; and a circuit for measuring and indicating the intercepted field; and an energy source. Field changes are constantly brought about by moving the probe or by sufficient capacitance changes in the capacitor.

The circuits of the present invention include a balancing circuit with a high-ohmic resistance, which ensures that the charges in the two plates of the capacitor remain opposite to each other at all times, so that a displacement of the charge is measured. The circuits also include filter stages, amplifier stages and circuits for evaluating and indicating the values measured.

As the values measured are small, care must be taken to ensure particularly satisfactory screening of all components, in order to reduce to a minimum the influence exerted on this sensitive apparatus by extraneous factos. The measuring electrode must therefore be screened particularly thoroughly, and it is desirable to also screen the connection cable and the housing. The screening system for the measuring electrode preferably includes a window through which the electrostatic field can reach the conductive measuring electrode. This window is positioned parallel to the surface of the organism to be evaluated.

In accordance with the present invention the electrostatic field can be continuously altered in various ways. In a first embodiment of the process the probe (i.e., the screened measuring electrode) is moved over the surface of the organism at a constant speed and at a constant distance therefrom. When differences occur in the charge concentration on the surface of the organism, a related change occurs in the electrostatic field in the capacitor (which is formed by the measuring electrode and by the surface of the organism and the air space therebetween) and the charge on the measuring electrode changes to equalize itself to that on the surface of the organism (equalize in magnitude, but opposite in sign). In this process, a current flows from or to the measuring electrode. This current is a measure of the charge concentration prevailing in the organism. As soon as the movement of the probe is stopped, however, and the electrical field is no longer changing, the charges are equal on the two plates of the capacitor but are of opposite sign, and no further current flows.

In another embodiment of the present invention, the changes in the field can be brought about by oscillating movements of the measuring electrode parallel to the surface of the organism within a fixed contactless probe or by the oscillating movement of a guard electrode.

In still another embodiment of the invention, the field changes can be brought about by altering the capacitance of the capacitor formed by the surface of the organism and the measuring electrode, either by varying the distance between the parts of the capacitor in an oscillatory movement or by modifying the dielectric constant of the capacitor.

The above discussed features and advantages of the present invention will be apparent to and understood by those skilled in the art from the following detailed description and drawings:

BRIEF DESCRIPTION OF THE DRAWINGS

Referring to the drawings, wherein like elements are numbered alike in the several FIGURES.

DESCRIPTION OF THE PREFERRED EMBODIMENTS

Figure 1:
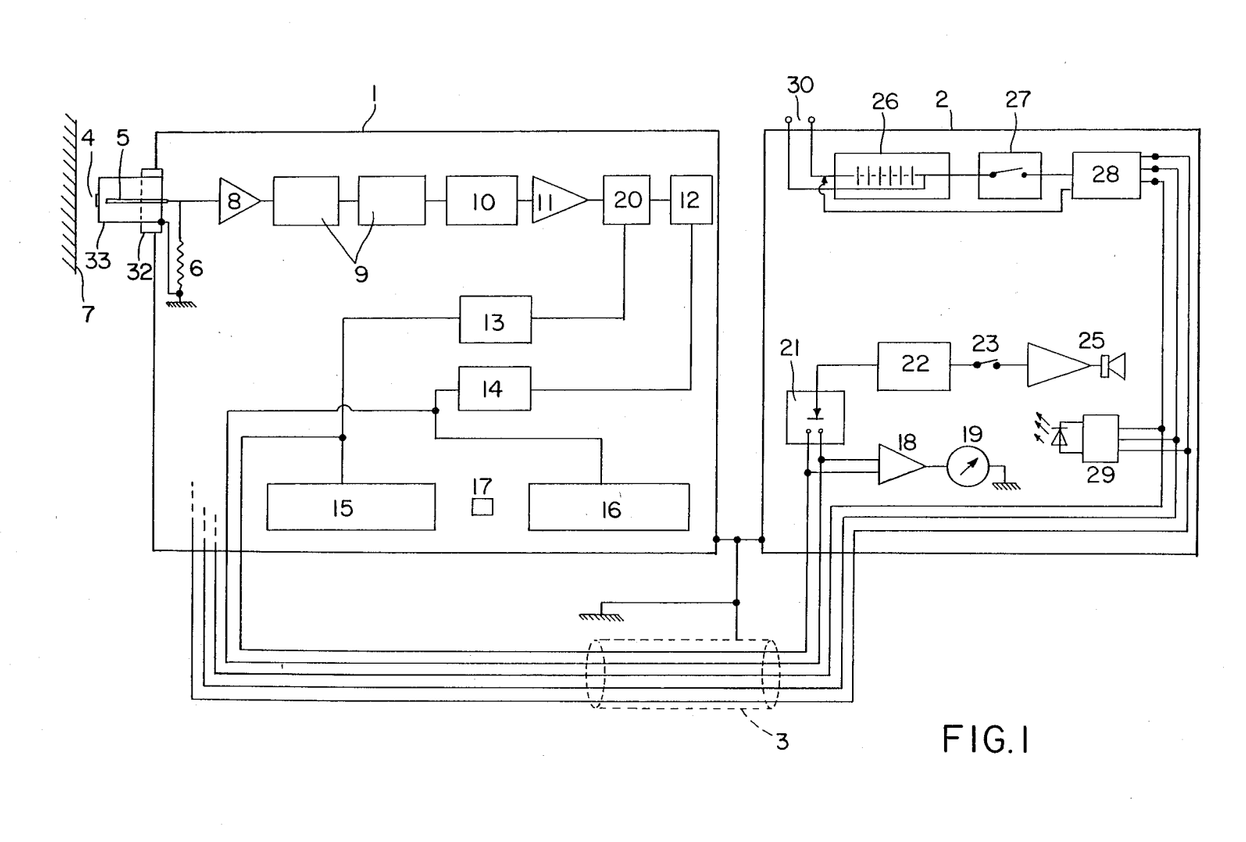
FIG. 1 is a block diagram of the apparatus of the present invention.

Referring to FIG. 1, a block diagram of the apparatus of the present invention is shown. The apparatus includes a first circuit section 1 in a separate housing and a second circuit section 2, which is also in a separate housing and which is connected to first circuit section 1 by a flexible screened cable 3. Circuit section 1 includes the probe, filter stages, amplification system and indicator system; while the circuit section 2 contains the measuring circuit and the energy source, all as set forth hereinafter. Circuit sections 1 and 2 could, of course, be combined in a single housing.

Figure 2:
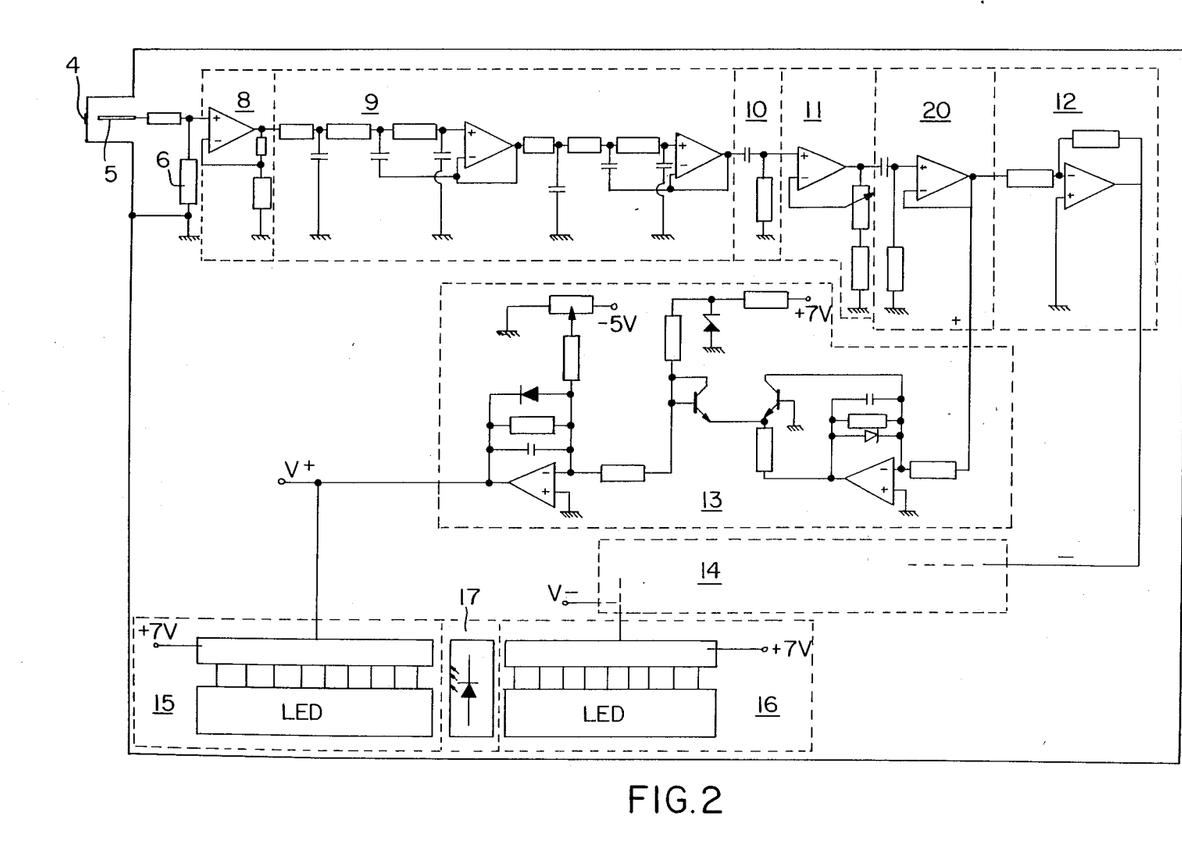
FIG. 2 is a schematic diagram of the first part of the apparatus of FIG. 1.

The probe of the embodiment of FIGS. 1 and 2 has an external screen 33 and a measuring electrode 5 of electrically conductive material, which is attached to but insulated from the screen 33 and from the housing. The measuring electrode 5 is mounted at one end in an opening in a wall 32 affixed to the housing of circuit section 1 and electrically insulated therefrom. Screen 33 is a metallic lining which surrounds the measuring electrode 5 all the way into the wall, leaving the free end of the measuring electrode exposed to and communicating with an electrostatic field via a window 4 parallel with the surface of the biological organism 7 which is to be measured.

Wall 32 is constructed so that the measuring electrode 5 and the screen 33 can be easily removed and replaced as a unit, e.g., with a screw plug, bayonet socket, clamp, etc.

It is also possible for non-conductive materials having a higher dielectric constant than air to be provided on the window 4, to increase the capacitance of the capacitor formed by the surface of the organism and by the free end of the electrode.

The probe is positioned close enough to the surface of the organism 7 to ensure that the level of charge on the measuring electrode 5 equalizes itself to the level of charge on the surface 7, while nevertheless being of opposite sign thereto. This results in electrons being attracted from or conducted away to ground. A current thus flows through the balancing resistor 6 from or to ground. The resistance 6 is very high, so a low current is sufficient to build up a voltage which is sufficient for the operation of amplifier 8.

The signals measured by the capacitance probe have a frequency of 0 to 10 Hz. The higher frequencies are cut off by filter 9 with 36 dB/Oct. This filters out undesirable electrical signals.

Figure 4:
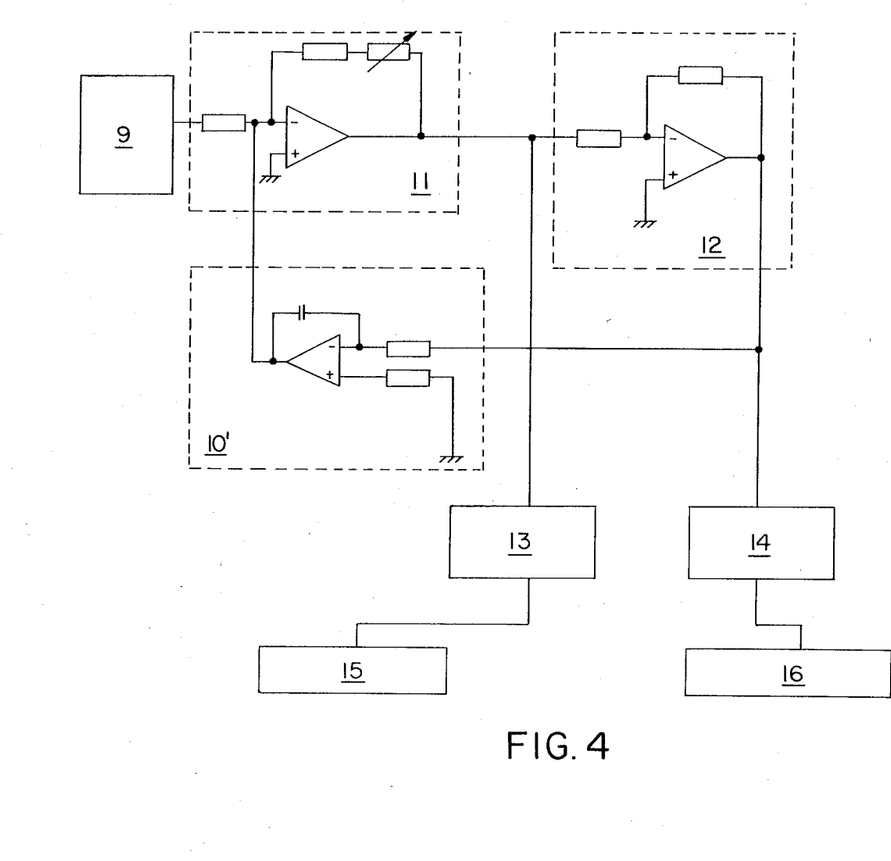
FIG. 4 shows a block diagram of an alternative version of the first part of the apparatus of FIG. 1.

High-pass filters 10 and 20 are provided to keep the measuring deflection of the apparatus independent of offset voltages caused in the amplifier stages. As shown in FIG. 2, this filtering property can be obtained by means of two differential circuits 10 and 20. In the embodiment of the invntion shown in FIG. 4, the same result can be obtained with an integration circuit in counter-coupling 10', although in this case the total number of components used is smaller.

Still referring to FIGS. 1 and 2, the signal from a filter 10 is amplified by the amplifier 11 and then subdivided, for further processing, into a positive and a negative signal in circuits 20 and 12. Both signals are amplified logarithmically, so that a weak signal is amplified by 50 dB more than a strong signal. The positive signal is delivered from circuit 20 to an amplifier 13 and is amplified logarithmically in amplifier 13. The negative signal is delivered from circuit 12 to an amplifier 14 and is also amplified logarithmically in amplifier 14. Luminous diodes (L.E.D.) connected, respectively to the outputs from amplifiers 15 and 16 indicate the signals separately. The zero state is continuously indicated by an additional diode 17 for guidance purposes.

Figure 3:
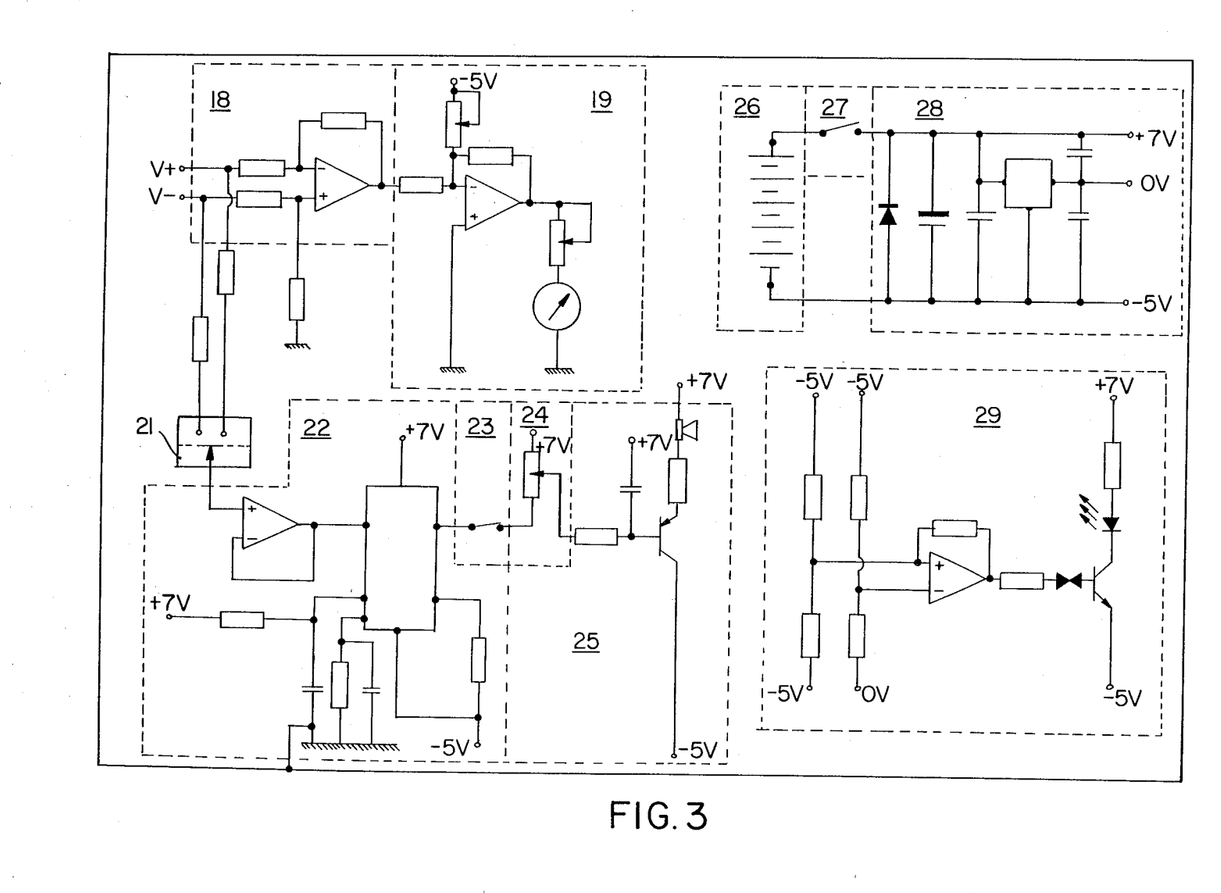
FIG. 3 is a schematic diagram of the second part of the apparatus of FIG. 1.

As shown in FIGS. 1 and 3, circuit section 2 of the apparatus contains an analog mA-meter 19 connected to receive a signal from a differential amplifier 18.

Circuit section 2 of the apparatus of the present invention includes a source of energy 26, preferably either a 12-V accumulator charger or a battery. By closing switch 27, the entire apparatus is supplied with energizing power. A rectifier 28 may also be included to stablize any fluctuating supply voltages between 10 and 12 V. An indicator light circuit 29 may also be included to show battery charge level.

It is also possible to produce, in addition, an acoustic signal, by closing a switch 21, whereby either the positive signal, the negative signal or both signals are delivered to an acoustic transducer or converter 22 which converts voltages into frequencies, so that the output frequency varies with voltage. The output of transducer 22 is delivered via switch 23 to an acoustic device 25 to sound an acoustic signal. An acoustic volume regulator can also be provided by means of a potentiometer 24. The acoustic device 25 can be switched off by means of a switch 23. The acoustic signal makes permanent visual monitoring of the indicator device unnecessary.

Figure 5:
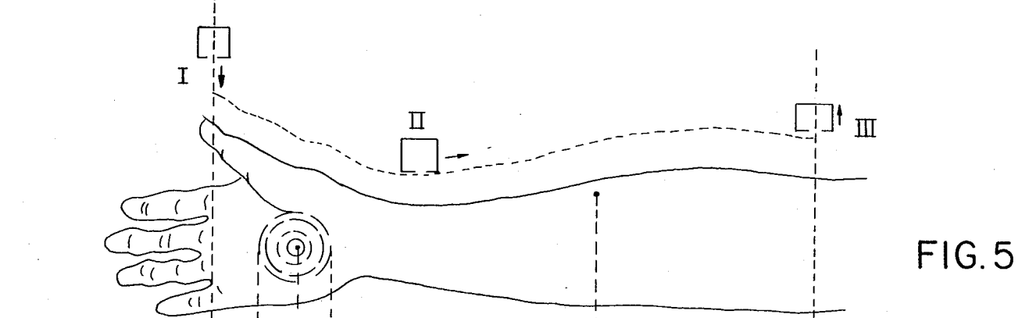
FIG. 5 shows the apparatus of the present invention in use in connection with part of a human body.
Figure 6:
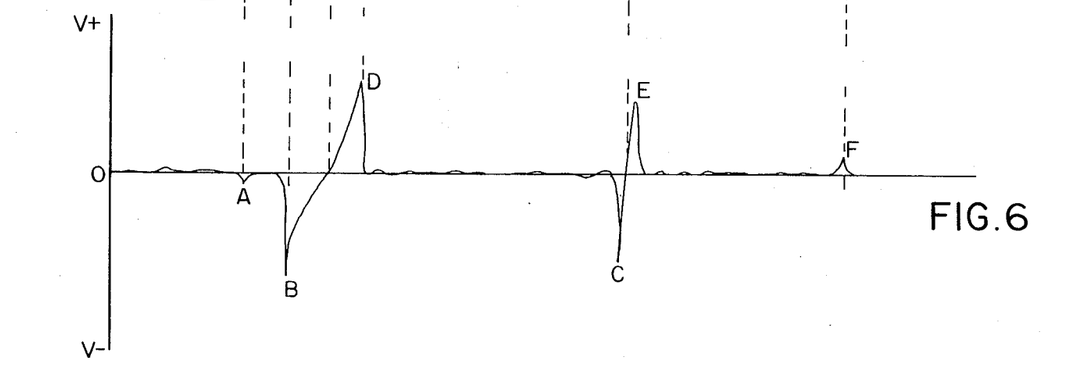
FIG. 6 shows a plot of output signals obtained from the FIG. 5 application.

Referring to FIGS. 5 and 6, an example of the operation of the process of the invention in use for the scanning of a forearm is presented.

In Position I the probe is moved close to the surface of the forearm. As son as the probe is sufficiently close thereto, preferably about 10 cm away, a first current flow through the high-ohmic resistor 6, to obtain the automatic zero setting (Position A in FIG. 6).

In Position II of FIG. 5, the hand has been scanned by the probe at a substantially constant separation distance. As soon as a point is approached at which a pathological process is taking place (shown by the swirl pattern in the hand), the voltage at resistor 6 will typically fluctuate over a range, such as B-D or C-E.

In Position III of FIG. 5, the probe is drawn away from the forearm on completion of the scan. The voltage, as shown at F in FIG. 6, changes in the opposite direction to A, as the capacitance of the capacitor is changed by the increasing distance.

The voltage changes are reflected by corresponding signals in a signal indicating device, such as meter 19. The deflection of the indicator at pathological points is clearly distinguishable from the remainder of the signals during the course of the scan.

The voltage diagram of FIG. 6 clearly shows, between B and D on the one hand and C and E on the other, two zones in which measurable voltages differences exist. In the wider zone between B and D an anomaly is observed in which a pathological process is taking place. It may be a recuperative process, such as the healing of a wound, or a focus of pain, such as a tumor.

The range between C and E points to a concentrated zone of greater activity. In this case it consists of a so-called acupuncture point.

The voltage diagram of FIG. 6, which constitutes a recording of an experimental measuring operation in accordance with the process of the present invention with the use of prototype apparatus of the present invention, immediately shows two important potential medical applications for the system. The first, as shown by the curve between C and D, is the accurate tracing of acupuncture points. The second is in tracing a pathological process, such as a focus of pain difficult to locate. It often occurs that with a general sensation of pain, the person in pain is not able to give any precise indication of the location of pain; and therefore the practitioner is not able to determine the cause of the pain or to diagnose it. A voltage diagram such as that of FIG. 6 enables the practitioner to fix the locus of the pain—e.g., the curve B-D. This is of particular value in the case of animals or even plants, which cannot give any information as to the locus of a pain or problem area.

The voltage diagram in FIG. 6 also shows, at A and F, that a movement perpendicular to the surface to be scanned sets up a signal. This could lead one to conclude that if the system were to be used for interference signals the probe in the measuring process would have to be guided parallel to the measuring surfaces, i.e., that a constant distance would have to be maintained. FIG. 6, however, shows that the amplitudes of the signals A and F are considerably smaller than those of the signals B-D and C-E, so that a deviation from the optimum scanning movement of a constant separation distance is not a serious problem. Because of its smaller amplitude, any interference signal generated by a small change in separation distance has no undesirable effect on a measuring signal A-D or C-E. That is, due to their respective amplitudes the measuring signals and the interference signals can very easily be distinguished from one another.

An important characteristic and feature of the process and of the apparatus shown in FIGS. 1-6 resides in the fact that it is potential or charge gradients that are measured and not absolute values. This automatically eliminates the interference factors to which other apparatus are subject, such as static electricity on the measuring surface, clothing, bandages, animal's fur, etc.

However, the absolute value of charge concentrations and potential differences can also be measured with one probe by causing the electrode 5 to form at one time a capacitor with the surface of the organism, and at another time a capacitor with an electrode at a known potential, in alternation, several times per period, with the probe stationary. This leads to continuous charge displacements, i.e., currents, which are a measure of the charge concentration prevailing on the surface of the organism. The interval of time elapsing between two successive measuring operations is naturally far shorter than the time constant in which the voltage signal leaves the measuring electrode, so that the momentary field intensity of each point on the surface of the organism can now be measured without contact.

In a modification of the invention, the probe can be supplemented by an infra-red or laser beam generator, so that the therapy points traced can be stimulated at the same time.

In a further modification, a current source can be connected to the screen 33 of the probe. This then serves as a contact electrode enabling use to be made of Dr. VOLL's well known method of therapy, which consists of the application to the body of the same form of current which it produces itself, in order to regulate the pathological tissue.

Figure 7:
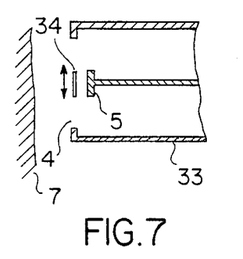
FIGS. 7-11 show alternative structures for the measurement probe of the present invention.

Referring now to FIG. 7, a modified version of the probe is shown. In this version the probe has a screen 33, a window 4, a measuring electrode 5 fixed in position in the probe, and a conductive movable guard electrode 34 which oscillates parallel to the surface 7 of the organism. When the guard electrode 34 is in the screening position shown in FIG. 7 the measuring electrode 5 forms a capacitor with the guard electrode 34, with the potential of electrode 5 being at the known potential of the guard electrode. When electrode 34 moves to a position in which the measuring electrode 5 is no longer covered by the guard electrode 34, the measuring electrode adapts itself to the potential of the surface 7 of the organism. The difference between these potentials is a measure of the charge concentration on the surface 7 of the organism and causes an electric current which can be measured.

Figure 8:
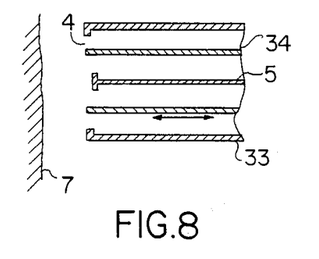

FIG. 8 shows another embodiment of an oscillating probe, in which the conductive guard electrode 34 encases the measuring electrode 5 and oscillates in the longitudinal direction. Depending on the position of the guard electrode 34, a greater or a smaller number of lines of force reach the measuring electrode 5. The operating principle is the same as in the embodiment of FIG. 7. The same effect can also be obtained by a rotating guard electrode 34.

The charge of the measuring electrode 5 is thus influenced by the capacitive coupling between the surface 7 of the organisms and the measuring electrode 5. At a constant potential on the surface 7 and with a stationary contactless probe, a charge displacement, which depends on the potential of the surface 7 of the organism, can be caused and measured. The charge displacement can likewise be brought about by a periodic alteration of the capacitor formed by the surface 7 of the organism and by the measuring electrode.

The modulation of this capacitance can be effected in various ways.

For example, the modulation can be obtained by the periodic alteration of the distance between the measuring electrode 5 and the surface 7 of the organism, the measuring electrode being caused to oscillate in the longitudinal direction for this purpose.

Figure 9:
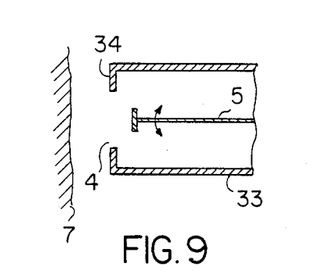

Also, in a further modification of the embodiments of FIGS. 7 and 8, a non-conductive guard electrode can be used, the dielectric constant of which differs from that of window 4. This provides a modulation of the dielectric constant of the capacitor. In FIG. 9, a further advantageous embodiment is illustrated, in which the dielectric constant is modulated by the periodic movement of the measuring electrode 5 parallel to the surface 7 of the organism.

Figure 10:
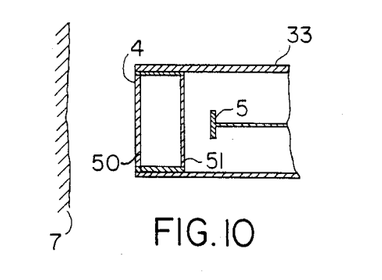

In another embodiment of the present invention, shown in FIG. 10, the probe consists of the measuring electrode 5, the screen 33 and the window 4, which contains an assembly of liquid crystals which are polarized by a modulation voltage on electrically conductive layers 50 and 51, the conductive layers being electrically insulated from the screen. The dielectric constant of the window 4 consisting of liquid crystals changes with the modulation voltage, since the material is characterized by the fact that it has a different dielectric constant at different polarizations.

Figure 11:
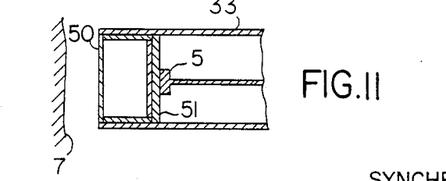

FIG. 11 shows still another embodiment which is a very compact version of FIG. 10. In FIG. 11, the measuring electrode 5 is affixed in an insulated position to the liquid crystal window 4.

Figure 12:
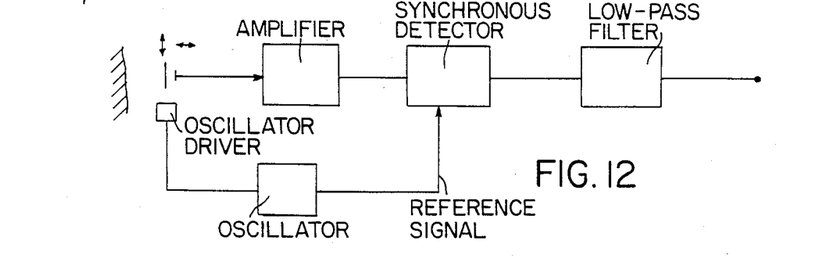
FIG. 12 shows a block diagram for use with an oscillating probe.

As shown in the block diagram provided in FIG. 12 the signal measured with a modulated probe can be amplified synchronously with a reference signal. This reference signal may emanate, for example, from an oscillator which also sets up the field modulation for the probe, or from a beam of light interrupted by a mechanical field modulator, or from capacitive receivers which indicate the position of a mechanical field modulator, or from inductive position or speed pick-ups or from a piezoelectric crystal of which the signal is a measure of the force applied to the mechanical field modulator.

Figure 13:
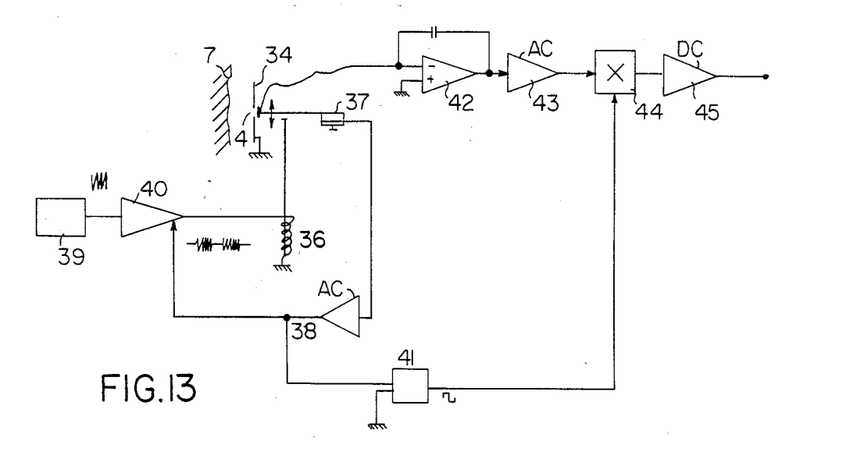
FIG. 13 shows a schematic of FIG. 12.
Figure 14:
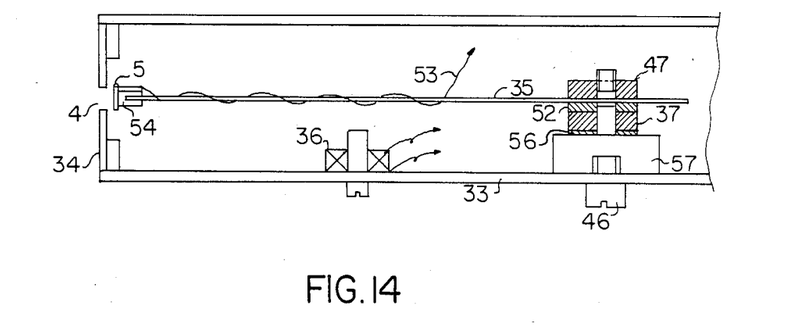
FIG. 14 shows details of a version of an oscillating probe.

Referring now to FIGS. 13 and 14, schematic and construction details are shown for the probe such as illustrated schematically in FIG. 9.

FIG. 13 contains a schematic circuit diagram for the probe of FIG. 9 and which can be appropriately connected to circuit sections 1 and 2 of FIGS. 1 and 2. This circuit of FIG. 13 can, however, also be adapted to the other probes hereof capable of modulation.

In the embodiment of FIGS. 13 and 14, the measuring electrode 5 is affixed in an electrically insulated position to the free end of a steel spring 35. This spring is clamped at its other end into a piezoelectric converter 37, the signals of which are amplified by an amplifier 38 in order to be conveyed to a modulator 40. Modulator 40 receives a high-frequency alternating voltage from an oscillator 39. This alternating voltage is modulated by a signal from the amplifier 38 and is transmitted to an electro-magnet 36. This electro-magnet attracts the steel spring 35. As the high frequency alternating voltage is considerably greater than the intrinsic frequency of the spring, the spring remains attracted by the electro-magnet. The movement in the spring is sensed by the converter 37, the signal of which, after amplification by amplifier 38, interrupts the alternating voltage 40 of high frequency. The steel spring 35 is then released to move back from the position to which it has been attracted, so that a self-sustained oscillating system is formed. By this oscillation the measuring electrode 5 is moved along the window 4 and its charge is influenced alternately by that of the surface of the organism or by that of a grounded guard electrode 54. The resulting charge displacements are converted by the charge amplifier 42 into an alternating voltage. This alternating voltage signal then passes through a band pass filter 43 which suppresses undesirable noise signals and offset voltages. The signal is then rectified in rectifier 44 synchronously with a reference signal, which is the signal from converter 37 as amplified in amplifier 38. In 41 the phases of the reference signal and of the amplifier 43 are coordinated with one another, in order to obtain an exact rectification at 44. After a further filtering operation at 45 the direct voltage is amplified, as described above, in conjunction with FIGS. 1, 2, 3 and 4.

The mechanical structure of the probe of FIG. 9 with an oscillating measuring electrode is shown in detail in FIG. 14. Within the screen 33, steel spring 35 is mounted in a metal bolt 46 which is affixed to the screen 33. This bolt has a bore into which the spring fits without touching the walls of the bore. The spring 35 is clamped between a nut 47 and a metal ring 52 which, in turn, rests on piezoelectric crystal 37. The crystal 37 forms part of the converter by which the vibrations of the spring 35 are converted into an electrical alternating voltage, which can be tapped by an electrode 56. The converter is grounded via the metal ring 52, the nut 47 and bolt 46. The electrode 56, however, is separated from the mass by an insulating ring. The intermediate spacer 57 enables the spring 35 to be adjusted to the exact height required in the bore, so that the spring 35 can transmit the oscillations of the piezoelectric crystal without coming into contact with the bolt. The properties of the spring 35 are selected to ensure that its intrinsic frequency will differ sufficiently from the power frequencies in the system and from their harmonics. Thus, the signal of the measuring electrode 5 can be separated from the power frequency interferences without difficulty. In an advantageous embodiment the intrinsic frequency of the spring 35 is about 80 Hz.

The screen 33 also contains, on its internal side and at an appropriate distance from the bolt 46, an electromagnet 36 serving to vibrate the spring 35. The screen 33 is separated from the surface of the organisms by a conductive guard electrode 34 with a centrally situated window 4, preferably circular in cross-section. The electrode 5 is affixed to the free end of the spring 35 by means of an insulating connector 54. An electric line 53 connects the electrode to the amplifer 42. The surface area of the measuring electrode 5 preferably coincides with the area of the window 4; and the diameter of the circular window is preferably equal to one quarter of the internal diameter of the screening system.

As distinguished from the embodiment shown in FIGS. 1-6 the essential characteristic of the embodiments shown in FIGS. 7-14 resides in the fact that absolute values are measured instead of gradient values.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for contactless measurement of charge concentration and potential differences in a biological organism, including the steps of:
   forming a capacitor having a measuring electrode as one plate of the capacitor and the surface of the biological organism as the other plate of the capacitor;
   moving one of said capacitor plates relative to the other to alter the electrostatic field and change the charge level on the measuring electrode as a function of charge levels in the biological organism;
   guiding the measurement electrode over the surface of the organism at a substantially constant distance therefrom; and
   monitoring the change in the charge on the measuring electrode to determine charge concentration in the biological organism.

2. A method for contactless measurement of charge concentration and Potential differences in a biological organism, including the steps of:
   forming a capacitor having a measuring electrode as one plate of the capacitor and the surface of the biological organism as the other plate of the capacitor;
   moving one of said capacitor plates relative to the other to alter the electrostatic field and change the charge level on the measuring electrode as a function of charge levels in the biological organism;
   oscillating said measuring electrode to alternatively form capacitors between said electrode and said surface of the organism and between said measuring electrode and a guard electrode; and
   monitoring the change in the charge on the measuring electrode to determine charge concentration in the biological organism.

3. A method for contactless measurement of charge concentration and potential differences in a biological organism, including the steps of:
   forming a capacitor having a measuring electrode as one plate of the capacitor and the surface of the biological organism as the other plate of the capacitor;
   moving one of said capacitor plates relative to the other to alter the electrostatic field and change the charge level on the measuring electrode as a function of charge levels in the biological organism;
   periodically varying the dielectric constant of the capacitor formed between said measuring electrode and said surface of the organism; and
   monitoring the change in the charge on the measuring electrode to determine charge concentration in the biological organism.

4. Apparatus for the contactless measurement of charge concentrations and potential differences in biological organisms, including:
   measuring electrode means for measuring charge concentrations;
   shield means for screening said electrode means and defining a window through which said electrode means is accessible to electrostatic fields;
   dielectric means in said window having a dielectric constant higher than air;
   said electrode means being one plate of a capacitor, the other plate of which is the surface of the organism to be measured;
   means for electrically connecting said electrode means to a reference potential;
   circuit means for measuring and/or indicating changes in charge on said electrode means resulting from relative movement of said electrode means with respect to said organism surface; and
   wherein said electrode means is centrally mounted within and insulated from said shield means, said electrode means communicating with said window and thereby means exposed to said electrostatic fields.

5. The apparatus of claim 4 wherein said circuit means includes:
   differential amplifier means for receiving signals from said electrode means; and
   meter means for displaying said signals.

6. The apparatus of claim 5, including:
   means for subdividing said signals from said electrode means into positive and negative signals; and
   means for logarithmically amplifying said positive and negative signals.

7. The apparatus of claim 4, including:
   acoustic signal means for generating acoustic signals commensurate with signals from said electrode means.

8. The apparatus of claim 4 including:
   guard electrode means, said electrode means and said organism surface forming a capacitor, and said first electrode means and said guard electrode means forming a second capacitor.

9. The apparatus of claim 8, including:
   means for moving said guard electrode relative to said electrode.

10. The apparatus of claim 9, wherein:
    said guard electrode surrounds said electrode and moves longitudinally with respect thereto.

11. The apparatus of claim 8, including:
    means for oscillating said electrode means relative to said guard electrode means.

12. The apparatus of claim 11 wherein:
    said electrode means is mounted on spring means, said spring means also being attached to piezoelectric means which generates signals in response to oscillation of said electrode means.

13. Apparatus for the contactless measurement of charge concentrations and potential differences in biological organisms, including:
    measuring electrode means for measuring charge concentrations;
    shield means for screening said electrode means and defining a window through which said electrode means is accessible to electrostatic fields;
    said electrode means being one plate of a capacitor, the other plate of which is the surface of the organism to be measured;
    means for electrically connecting said electrode means to a reference potential; and circuit means for measuring and/or indicating changes in charge on said electrode means resulting from relative movement of said electrode means with respect to said organism surface;

means for periodically varying the dielectric field between said electrode means and said organism surface; and wherein said electrode means is centrally mounted within and insulated from said shield means, said electrode means communicating with said window and thereby being exposed to said electrostatic fields.

14. The apparatus of claim 13 wherein:

said varying means includes means for moving a dielectric guard electrode between the surface of the organism and said electrode means.

15. The apparatus of claim 13 wherein:

said varying means includes means for moving said electrode means relative to a dielectric guard electrode.

16. The apparatus of claim 13 including:

liquid crystal means between said electrode means and said organism surface, and means for varying the polarization of said liquid crystal means.

17. The apparatus of claim 16 wherein:

said electrode means is fixed to and insulated from said liquid crystal means.

18. A method for contactless measurement of charge concentration and potential differences in a biological organism, including the steps of:

forming a capacitor having a measuring electrode as one plate of the capacitor and the surface of the biological organism as the other plate of the capacitor;

moving the capacitor plate which includes said measuring electrode relative to the surface of the biological organism to alter the electrostatic field and change the charge level on the measuring electrode as a function of charge levels in the biological organism; and monitoring the change in the charge on the measuring electrode to determine charge concentration in the biological organism.

19. The method of claim 18 wherein the step of moving a capacitor plate includes:

guiding the measurement electrode over the surface of the organism at a substantially constant distance therefrom.

20. The method of claim 18 including:

oscillating said measuring electrode to alternatively form capacitors between said electrode and said surface of the organism and between said measuring electrode and a guard electrode.

21. The method of claim 18 further including:

periodically varying the dielectric constant of the capacitor formed between said measuring electrode and said surface of the organism.

* * * * *